(12) United States Patent
Nakagawa

(10) Patent No.: US 8,172,398 B2
(45) Date of Patent: May 8, 2012

(54) UNIT FOR OBTAINING AND DISPLAYING FUNDUS IMAGE

(75) Inventor: Toshiaki Nakagawa, Tokyo (JP)

(73) Assignee: Kowa Company, Ltd., Aichi (JP)

( * ) Notice: Subject to any disclaimer, the term of this patent is extended or adjusted under 35 U.S.C. 154(b) by 193 days.

(21) Appl. No.: 12/824,535

(22) Filed: Jun. 28, 2010

(65) Prior Publication Data

US 2011/0032478 A1    Feb. 10, 2011

(30) Foreign Application Priority Data

Jul. 8, 2009    (JP) .................................. 2009-161466

(51) Int. Cl.
*A61B 3/14*    (2006.01)
*G06K 9/00*    (2006.01)

(52) U.S. Cl. .................... 351/206; 351/205; 382/154

(58) Field of Classification Search .......... 351/200–246; 345/419, 582, 583, 629; 382/154; 396/18; 356/12

See application file for complete search history.

(56) References Cited

U.S. PATENT DOCUMENTS

| | | | | |
|---|---|---|---|---|
| 6,575,571 | B2 * | 6/2003 | Shibata | 351/206 |
| 6,893,128 | B2 * | 5/2005 | Mizukusa et al. | 351/206 |
| 7,549,746 | B2 * | 6/2009 | Tsukada et al. | 351/206 |

FOREIGN PATENT DOCUMENTS

| | | |
|---|---|---|
| JP | H11-151206 | 6/1999 |
| JP | 2003-024279 | 1/2003 |
| JP | 2004-159767 | 6/2004 |

* cited by examiner

*Primary Examiner* — Mohammed Hasan
(74) *Attorney, Agent, or Firm* — Duane Morris LLP

(57) ABSTRACT

Unit for obtaining and displaying fundus image is comprised of a memory that stores a plurality of fundus images wherein a positional relation between an optical axis of an eye ball being examined and an optical axis of an objective is different, an image playback portion for producing a three-dimensional pseudo image by repeatedly displaying a plurality of fundus images on a display in order for a display time set on each fundus image, a CUP contour position designating means for designating a CUP contour position on the three-dimensional pseudo image, means for specifying the CUP contour position designated on the three dimensional pseudo image based upon a specific fundus image, and means for computing CUP contour based upon the specified CUP contour CD position and means for displaying the computed CUP contour.

3 Claims, 5 Drawing Sheets

(a) NORMAL (b) SL [CASE OF RIGHT EYE]

(c) SR [CASE OF RIGHT EYE]

UNIT FOR OBTAINING AND DISPLAYING FUNDUS IMAGE

CROSS REFERENCE TO RELATED APPLICATION

The present disclosure relates to subject matter contained in Japanese patent application No. 2009-161466 filed on Jul. 8, 2009, the disclosure of which is expressly incorporated herein by reference in its entirety.

BACKGROUND OF THE INVENTION

The invention relates to a unit for obtaining and displaying fundus image that can display a pseudo three-dimensional fundus image by alternately displaying two or more fundus images wherein optical axes are slightly shifted, and especially relate to a unit for obtaining and displaying fundus image for properly designating a position of a CUP on the fundus image three-dimensionally displayed.

When three-dimensionally watching the fundus image, a known unit for obtaining and displaying fundus image is conventionally used and in such a unit, two sheets of fundus images are obtained for the same eye to be examined from a point where optical axes of the eye to be examined and a fundus camera are slightly shifted, and a three-dimensional fundus image can be falsely displayed by alternately displaying these two fundus images (see Japanese patent application the publication number of which is 2003-24279). Then, observers, such as patients, examiners and doctors, feel a solidity in an explanation at the time of obtaining informed consent with a three-dimensional fundus image displayed in the unit for obtaining and displaying fundus image in comparison with an explanation with a normal two-dimensional image, and such an explanation with the three-dimensional image is extremely easy to be understood.

One of ophthalmic diseases is glaucoma. In glaucoma, optic nerve is destroyed and visual field is defective, so that glaucoma may cause loss of eyesight. A well-known method for testing glaucoma is to check a state of excavation of a disc, and in one of such methods, a C/D ratio (cup-to-disc ratio) is an index (see Japanese patent application publication number of which is H11-151206).

In order to compute a C/D ratio, it is necessary to measure an outer periphery of a cup and a diameter of an outer periphery of a disc from the fundus image.

When determining outer peripheries of a cup and a disc while watching the fundus image, the outer periphery of the disc is relatively easily determined even on the normal two-dimensional image since a difference between its periphery and its luminance is large, but the outer periphery of the cup is not easily determined from the normal two-dimensional image since a dent portion is necessary to be seen through. Therefore, an error of the C/D ratio may be large between the examiners, and diagnosis results of glaucoma may be different between the examiners thereby.

In order to solve such a problem, such a method is considered that a pseudo three-dimensional image is displayed by making use of technique of Japanese patent application publication No. 2003-24279 in order to determine the outer periphery of the cup on the image.

In a case where a position of a CUP is designated on a plurality of fundus images that are alternately displayed by such kind of the unit of obtaining and displaying fundus image, a designation subject is on different points on a plurality of fundus images and movements occur. If such a movement is large, it is difficult to designate. This is because the fundus images where optical axes of the fundus camera are slightly shifted are alternately displayed in order to falsely three-dimensionally display the fundus image. Even if the movement is small, the examiner does not know which point should be designated on the alternately displayed fundus images where the optical axes are shifted and is confused, and hesitates to designate the position.

Then, an object of the invention is to provide a unit for obtaining and displaying fundus image for properly designating a specific position on an image, displaying a three-dimensional image, as well as for displaying a three-dimensional pseudo fundus image by alternately displaying a plurality of fundus images wherein optical axes are slightly shifted.

SUMMARY OF THE INVENTION

One aspect of the invention is unit for obtaining and displaying fundus image, comprising:
  a display;
  a means for obtaining fundus image, having an objective;
  a memory means for storing a plurality of fundus images concerning the same eye to be examined, obtained through said means for obtaining fundus image, where positional relations between an optical axis of an eyeball of said eye to be examined and an optical axis of said objective are different from each other;
  an image playback portion for repeatedly displaying a plurality of fundus images stored in said memory means in order on said display for a time set on each said fundus image so as to produce a three-dimensional pseudo image;
  a CUP contour position designating means for designating a CUP contour position on said three-dimensional pseudo image that is displayed on said display;
  a position specifying means for specifying said CUP contour position designated on said three-dimensional pseudo image based upon a specific fundus image of said plurality of fundus images;
  a CUP contour computing means for computing a CUP contour based upon said specified CUP contour position; and
  a position displaying means for displaying said computed CUP contour on said specific fundus image.

According to this aspect of the invention, the position specifying means specifies the CUP contour position designated on the three dimensional pseudo image based upon the specific fundus image of a plurality of fundus images, so that it is sufficient for the operator to designate the CUP contour position based on the specific fundus image. Therefore, it is easily designate the CUP contour position on the three dimensional pseudo image.

The other aspect of the invention is the unit for obtaining and displaying fundus image, wherein said display time that is set on said specific fundus image is longer than one of the other fundus image.

According to this aspect of the invention, if the display time of the specific fundus image is longer than the other fundus images, an operator tends to designate the CUP contour position based upon the specific fundus image displayed for the longer time. Then, it is easy for the operator to designate the CUP contour position on the three dimensional pseudo image by specifying the CUP contour position on the three dimensional pseudo image based upon the specific fundus image displayed for the longer time.

Another aspect of the invention is the unit for obtaining and displaying fundus image, further comprising a DISC contour extracting means for respectively extracting DISC contours from said plurality of fundus images obtained through said means for obtaining fundus image and storing the extracted in said memory means;

whereby said image playback portion:

can produce the three-dimensional pseudo image by repeatedly displaying at least two fundus images on said display in order for the display time set on each fundus image; and has an image position determining means for determining a relative position of said two fundus images at the time when continuously displaying said at least two fundus images in order on the display so as to correspond the DISC contours between both fundus images continuously displayed with each other; and said image playback portion produces said three-dimensional pseudo image by displaying said both fundus images so as to correspond said DISC contours of both with each other based upon said relative position of both fundus images determined by said image position determining means.

According to this aspect of the invention, the shift of positions of the optical axes between two fundus images is the minimum in the DISC contour portion in appearance since the DISC contours of two fundus images continuously displayed are corresponded with each other, and amount of the movement of the CUP contour CD that is positioned at the back rather than the DISC contour can be made small also. Therefore, it is easily designate the position of the CUP contour.

Besides, the luminance of the fundus image is widely changed between inside and outside of the DISC contour, so that an extracting procedure of the DISC contour can be easily and accurately performed. And, it is possible to produce the image wherein the movement of the DISC contour is small when displaying the three-dimensional pseudo image based upon the DISC contour thereafter. Therefore, it is possible to display the three-dimensional pseudo image on which the position of the CUP contour rather inside of back of the DISC contour can be easily designated.

DESCRIPTION OF THE PREFERRED EMBODIMENTS

Embodiment of the invention will now be explained, referring to appended figures.

Figure 1:
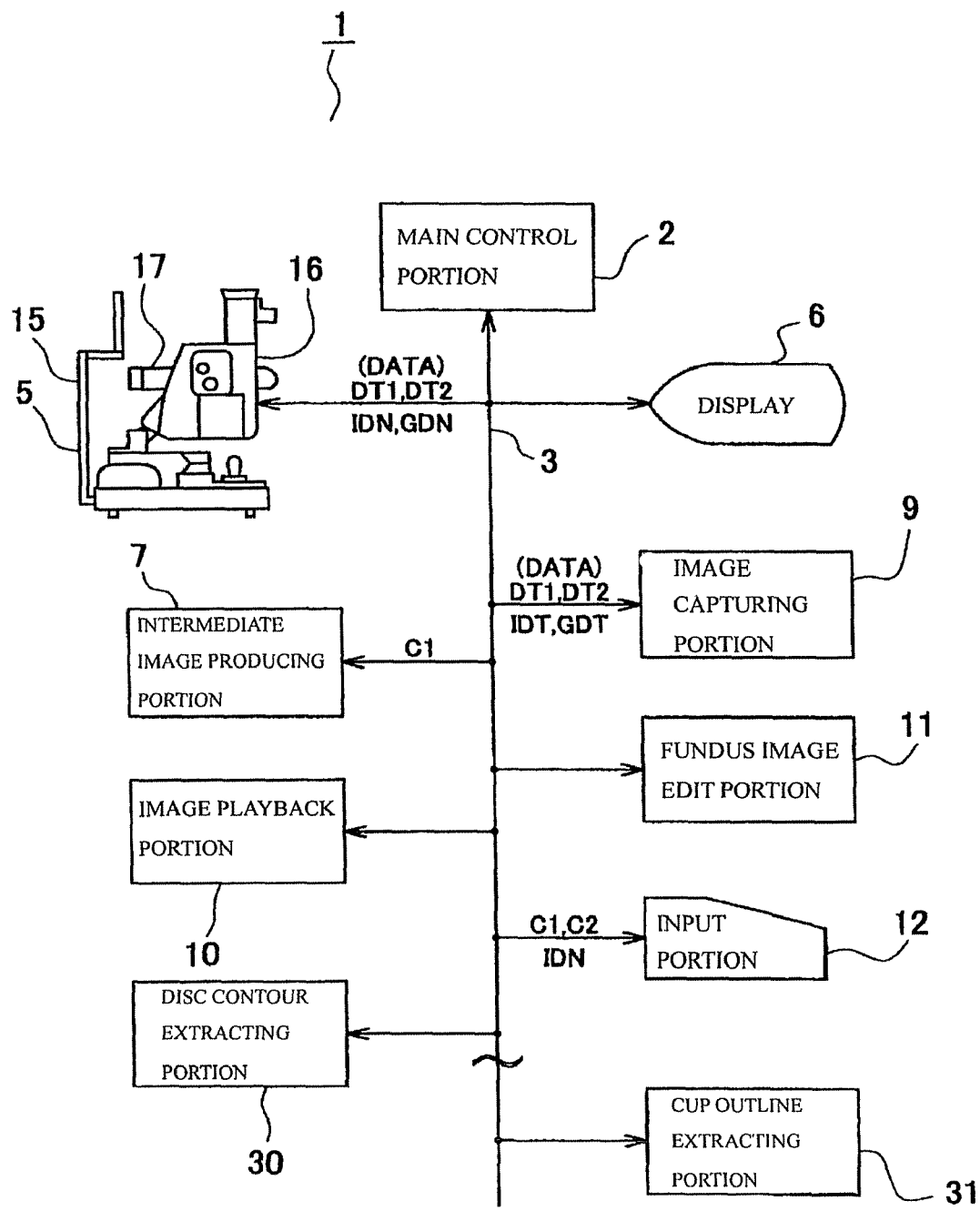
FIG. 1 is a block diagram that shows an example of a unit for obtaining and displaying fundus image to which the invention is applied.

As shown in FIG. 1, a unit for obtaining and displaying fundus image 1 has a main control portion 2, and a fundus camera 5, a display 6, an intermediate image producing portion 7, an image capturing portion 9, an image playback portion 10, a fundus image edit portion 11, an input portion 12 comprised of a keyboard and a mouse, a DISC contour extracting portion 30, and a CUP contour extracting portion 31 are connected with the main control portion 2 through a bus line 3.

Figure 5:
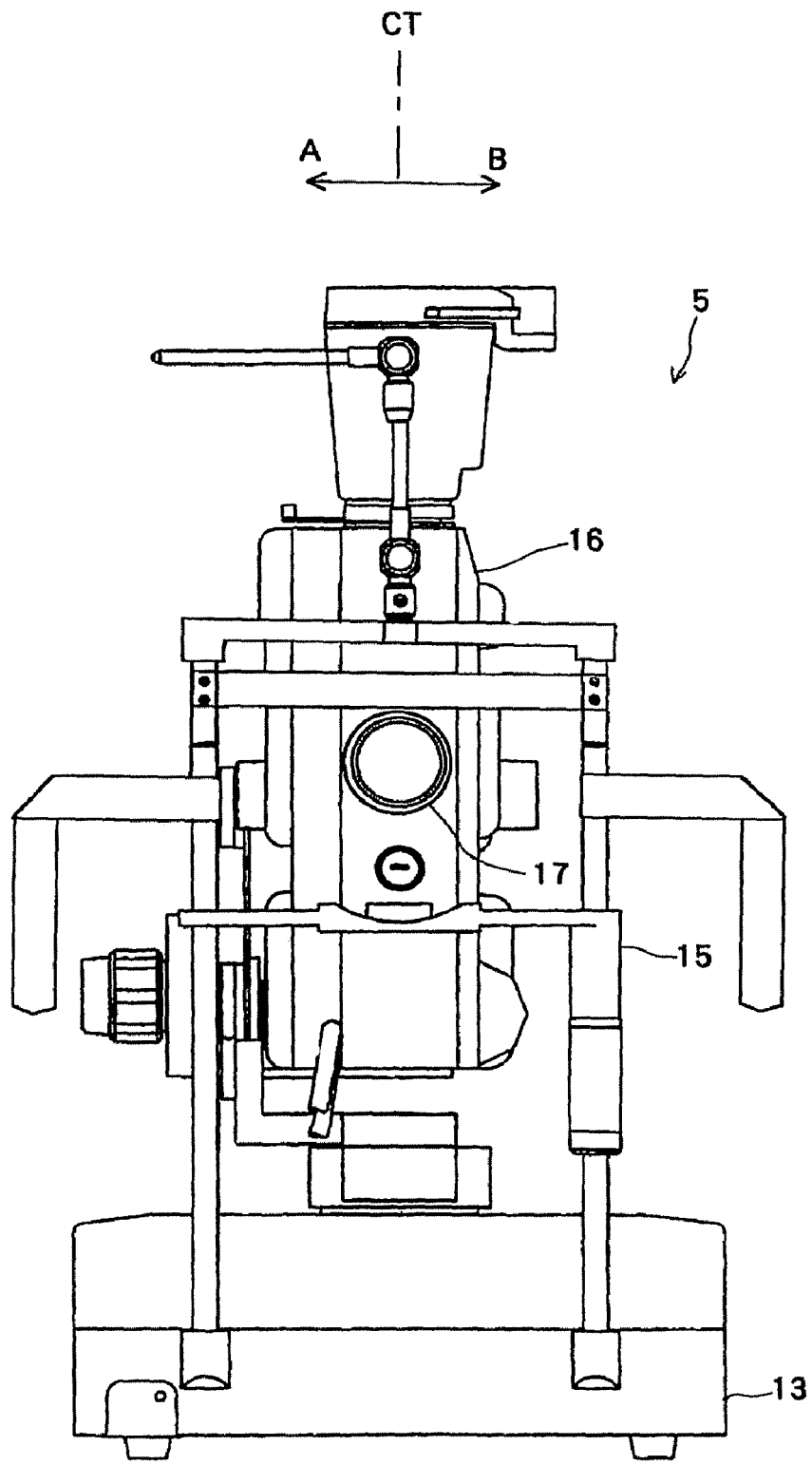
FIG. 5 is a view of an example of a front view of a fundus camera.

As shown in FIG. 5, the fundus camera 5 has a base 13, and the base 13 is provided with a jaw support 15 so as to support a face of an examinee on a camera body 16. The base 13 is provided with the camera body 16 so as to be free to move within predetermined bounds in a horizontal direction, that is, in a direction as shown by arrows A and B in the figure, and the camera body 16 is provided with an objective lens 17, facing to an eye to be examined of an examinee.

Figure 2:
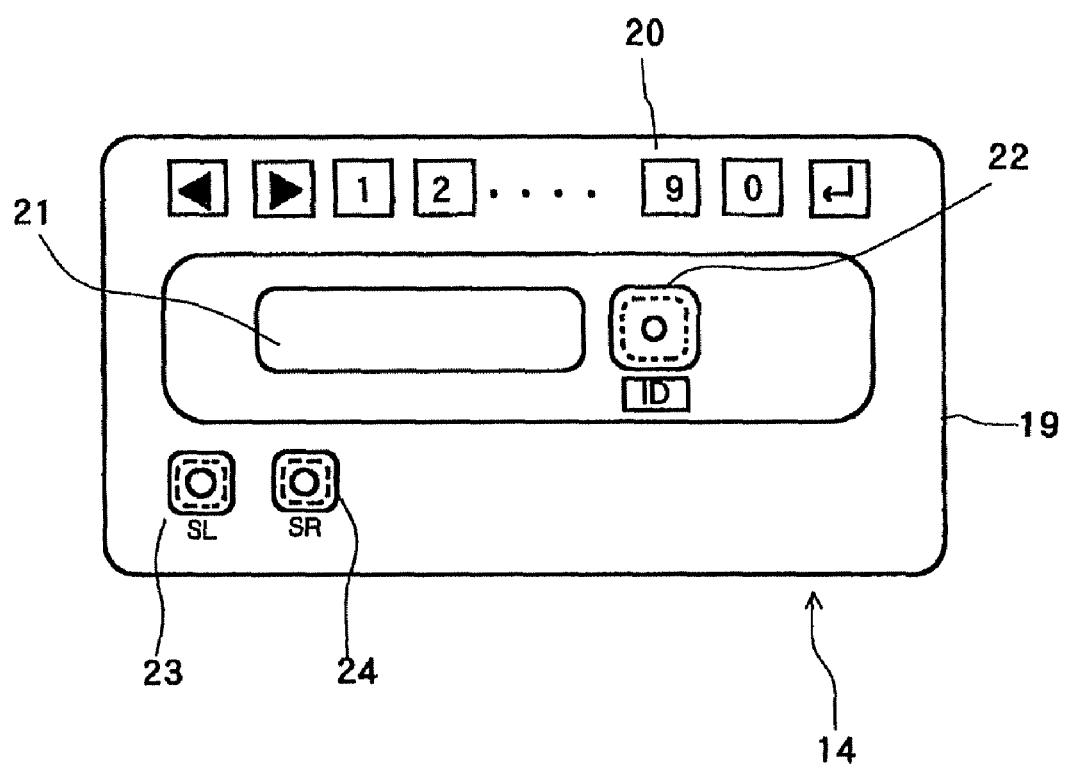
FIG. 2 is a schematic drawing of an operation panel.

As shown in FIG. 2, the base 13 is provided with an operation panel 14, and the operation panel 14 is provided with a ten key 20, a display 21, an ID switch 22 and stereo photography buttons 23, 24. The other many members, such as an input key and a switch, are actually provided on the operation panel 14. But, the members having no direct relation with the invention are not shown in the figure.

In order to obtain fundus images of an examinee with the unit for obtaining and displaying fundus image 1 having the above-mentioned structure, a jaw of an examinee is put on the jaw support 15 so as to face an eye to be examined to the camera body 16. Subsequently, the examiner moves the camera body 16 in a direction as shown by the arrow A or B of FIG. 5 so as to face a right eye or a left eye of the examinee to objective lens 17 of the camera body 16.

In order to obtain the fundus image of the right eye of the examinee, the camera body 16 is moved in the direction as shown by the arrow B with respect to center position CT in its right and left direction, and in order to obtain the fundus image of the left eye of the examinee, the camera body 16 is moved in the direction as shown by the arrow A with respect to the center position CT in its right and left direction, as shown in FIG. 5. Then, if proper means, such as a sensor, detects a moving form of the camera body 16 with respect to the center position CT, it is possible to immediately recognize for which eye, the right one or left one, the fundus image is to be obtained by the fundus camera 5.

Figure 3:
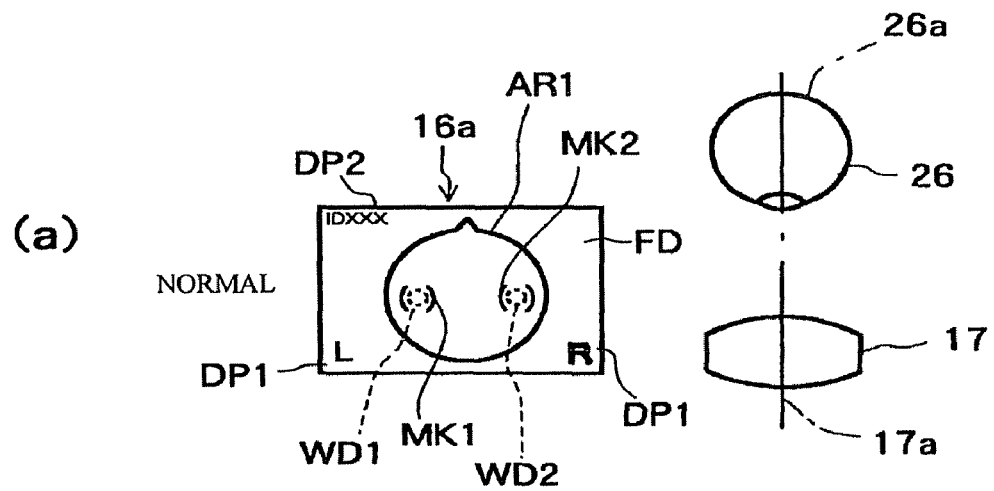
FIG. 3 is views that show relations between an eye to be examined and an optical axis of a lens when obtaining the fundus image and examples of finder images at such times.
Figure 3:
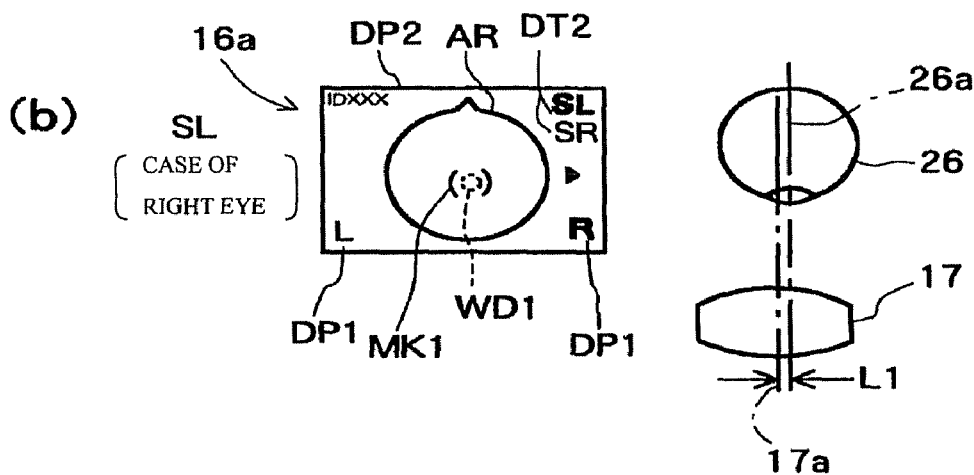
Figure 3:
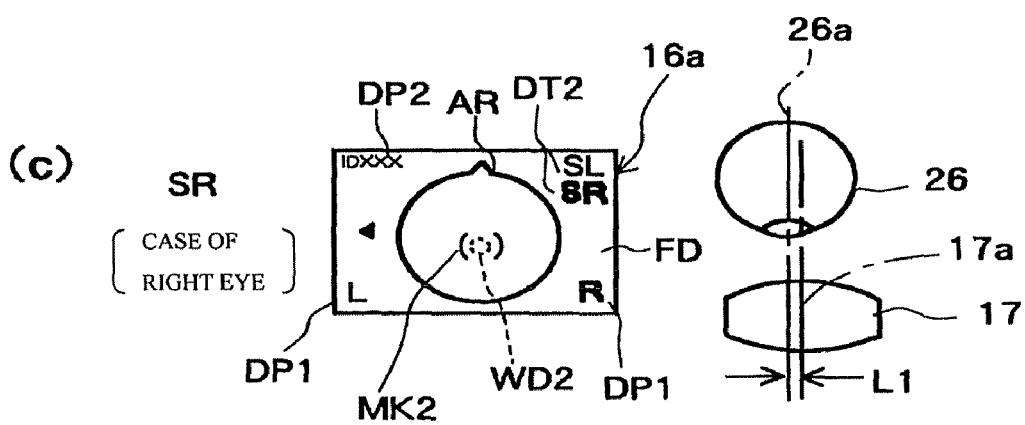

Examined eye data DT1 showing right or left of the examined eye that has been detected through a sensor, that has been judged based upon the position of the camera body 16 with respect to the center position CT of the camera body 16 is outputted to the image capturing portion 9, and a bold character "R" that shows the right eye of "R" showing the right eye and "L" showing the left eye that are right/left eye indication DP1 of the visual field FD inside a finder 16a of the camera body 16 as shown in FIG. 3 is displayed for instance. Then, it is understandable that the fundus image to be obtained from now on is the image on the right eye of the examinee.

In order to obtain a normal fundus image of the examinee through the fundus camera 5, the examinee presses a button of the operation panel 14 (not shown) for instructing to obtain a normal fundus image, and inputs an instruction for obtaining a normal fundus image from now on in the fundus camera 5. Then, an indication DP2 for inputting an identification number of the examinee flashes on the field FD and invites to input the identification number of the examinee through the ten key 20 or the like.

Then, when the examiner presses the ID switch 22 of the operation panel 14 and inputs the identification number IDN of the examinee through an operation of the ten key 20, the inputted identification number IDN is displayed on an indication DP2 in the field FD and is notified to the image capturing portion 9.

In case of the normal fundus image, it is necessary to obtain the fundus image in such a state that an optical axis 26a of an eye ball 26 is corresponded with an optical axis 17a of the objective lens 17, as shown in FIG. 3 (a). In order to do so, positioning marks MK1 and MK2, for positioning, are displayed on both right and left sides in a pixel obtaining area AR1 having a circular shape where the fundus image is to be obtained on the field FD of the fundus camera 5, and both light spots WD1 and WD2 for positioning, provided respectively corresponding to the positioning marks MK1 and MK2, are displayed. Then, the examiner slightly moves the camera body 16 in the direction as shown by the arrows A and B and in an up and down direction of FIG. 5 so as to include the light spots WD1 and WD2 inside the marks MK1 and MK2 such that the camera 16 is positioned, corresponding the optical axis 26a of the eye ball 26 with the optical axis 17a of the objective lens 17. But, the method of corresponding the optical axis 26a of the eye ball 26 and the optical axis 17a of the objective lens 17 with each other with the positioning marks MK1 and MK2 and the light spots WD1 and WD2 is not mentioned since such a method is a well-known.

After thus corresponding the optical axis 26a of the eye ball 26 and the optical axis 17a of the objective lens 17 with each other, photographing beams, such as strobes, are injected into the eye ball 26 from the camera body 16 so as to obtain the fundus image. An obtained front fundus image SFV where the optical axis 26a of the eye ball 26 and the optical axis 17a of the objective lens 17 are corresponded with each other is outputted to the image capturing portion 9 as fundus image data GDT. "The front image" in the specification means the fundus image taken in such a state that the optical axis 26a of the eye ball 26 and the optical axis 17a of the objective lens 17 are corresponded with each other, "left image" means the fundus image taken in such a state that the optical axis 17a of the objective lens 17 is shifted in a left direction with respect to the optical axis 26a of the eye ball 26, and "right image" means the fundus image taken in such a state that the optical axis 17a of the objective lens 17 is shifted in a right direction with respect to the optical axis 26a of the eye ball 26.

If the fundus image to be obtained from now on is a stereo image, the examiner inputs the above-mentioned identification number IDN, and thereafter, presses down the stereo photography button 23 shown as "SL" in FIG. 2 of the operation panel 14.

Then, the fundus camera 5 is switched into a stereo left image photographing mode. Such a stereo left image photographing mode is the photographing mode in such a state that the optical axis 17a of the objective lens 17 is shifted slightly small distance L1 on the left side with respect to the optical axis 26a of the eye ball 26 as shown in FIG. 3 (b).

If the stereo photography button 23 is pressed down, "SL" showing that the fundus image to be obtained from now on is the left side image of the stereo image is indicated in bold letters as shown in FIG. 3 (b), and the stereo designation information DT2, such as "SL" is outputted to the image capturing portion 9. When obtaining the normal fundus image wherein the optical axis 26a of the eye ball 26 and the optical axis 17a of the objective lens 17 are corresponded with each other, that is, the front fundus image SFV, the stereo designation information DT2 has no designation (for instance, "zero").

In such a stereo left image photographing mode, only positioning mark MK1 for positioning is indicated in a center of the circular pixel obtaining area AR1 where the fundus image should be obtained on the visual field FD of the fundus camera 5. In other words, in the photography in such a state that the optical axis 26a of the eye ball 26 and the optical axis 17a of the objective lens 17 are corresponded with each other, the positioning mark MK1 that has been located on the left side in the pixel obtaining area AR1 is located at the center, so that the examiner slightly moves the camera body 16 in the direction as shown by the arrows A and B and in the up and down direction in FIG. 5 so as to store the corresponding light spot WD1 for positioning in the positioning mark MK1. Then, the camera body 16 is positioned in such a state that the optical axis 17a of the objective lens 17 is shifted a slight distance L1 on the left side with respect to the optical axis 26a of the eye ball 26.

Since it is sufficient for the examiner to adjust the position of the camera body 16 so as to store the light spot WD1 for positioning in the corresponding positioning mark MK1, the positioning is extremely simple.

After the camera body 16 was thus positioned in such a state that the optical axis 17a of the objective lens 17 is shifted a slight distance L1 on the left side with respect to the optical axis 26a of the eye ball 26, photographing beams, such as strobes, are injected into the eye ball 26 from the camera body 16 so as to obtain the left stereo fundus image SLV. The thus obtained left stereo fundus image SLV is outputted to the image capturing portion 9 as the fundus image data GDT.

Subsequently, the examiner presses down the stereo photography button 24 on which "SR" is indicated in FIG. 2 of the operation panel 14.

Then, the fundus camera 5 is switched into the right stereo photographing mode. Such a right stereo photographing mode is one in such a state that the optical axis 17a of the objective lens 17 is shifted a slight distance L1 on the right side with respect to the optical axis 26a of the eye ball 26, as shown in FIG. 3 (c).

When the stereo photography button 24 being pressed down, "SR" showing that the fundus image to be obtained from now on is the right side image of the stereo, image is indicated in bold letters, and the stereo designation information DT2, such as "SR" is outputted to the image capturing portion 9.

In such a right stereo photographing mode, only positioning mark MK2 for positioning is indicated in the center of the circular pixel obtaining area AR1 where the fundus image should be obtained on the visual field FD of the fundus camera 5. In other words, in the photography in such a state that the optical axis 26a of the eye ball 26 and the optical axis 17a of the objective lens 17 are corresponded with each other, the positioning mark MK2 that has been located on the right side in the pixel obtaining area AR1 is located at the center, so that the examiner slightly moves the camera body 16 in the direction as shown by the arrows A and B and in the up and down direction in FIG. 5 so as to store the corresponding light spot WD2 for positioning in the positioning mark MK2. Then, the camera body 16 is positioned in such a state that the optical axis 17a of the objective lens 17 is shifted a slight distance L1 on the right side with respect to the optical axis 26a of the eye ball 26.

Since it is sufficient for the examiner to adjust the position of the camera body 16 so as to store the light spot WD2 for positioning in the corresponding positioning mark MK2, the positioning is extremely easy.

After the camera body 16 was thus positioned in such a state that the optical axis 17a of the objective lens 17 is shifted a slight distance L1 on the right side with respect to the optical axis 26a of the eye ball 26, photographing beams, such as strobes, are injected into the eye ball 26 from the camera body 16 so as to obtain the right stereo fundus image. The thus obtained right stereo fundus image SRV is outputted to the image capturing portion 9 as the fundus image data GDT.

The left stereo fundus image SLV and the right stereo fundus image SRV outputted to the image capturing portion 9 may be outputted, including the indication DP2 of the identification number IDN of the examinee and the indication, such as "SL" and "SR" of the stereo designation information DT2 that are displayed on the visual field FD of the finder 16a therein as image information, as well as the fundus image (This is the same for the front fundus image SFV).

The photographing data DATA for some eye to be examined that was captured by the image capturing portion 9, such as the examined eye data DT1, the identification number IDN and the stereo designation information DT2, is stored in a predetermined memory area as binary data. At this time, the fundus image edit portion 11 edits the stored photographing data DATA and the fundus image data GDT, such as the the left stereo fundus image SLV and the right stereo fundus image SRV so as to relate with each other and the edited data is stored in a predetermined memory area. This is the same in case of the front fundus image SFV.

When some fundus image data GDT is read out of the memory area, the corresponding photographing data DATA is also immediately read out and the fundus image data GDT is specified. On the contrary, by inputting the photographing data DATA, the corresponding fundus image data GDT can be searched and read out. In a case where the indication DP2 of the identification number IDN of the examinee and the indication, such as "SL" and "SR" of the stereo designation information DT2 that are indicated on the visual field FD of the finder 16a are captured into the fundus image data GDT as well as the fundus image, when reading the fundus image data GDT, the corresponding photographing data DATA is immediately made apparent on the image, so that it is convenient. If the photographing data DATA is stored as binary data as mentioned before, the binary data can be immediately used for the other electronic testing devices. In addition, if the photographing data DATA on the image is converted into binary information with well-known character recognition means, each fundus image data GDT can be arranged and stored. In such a case, if the fundus camera 5 merely outputs the fundus image data GDT in which the photographing data DATA is taken to the image capturing portion 9, the image capturing portion 9 reads the photographing data DATA by character recognition from the fundus image data GDT, and stores in the memory means, relating to the fundus image data GDT. Therefore, it is not necessary to output the photographing data DATA excluding the fundus image data GDT from the fundus camera 5, and data transmission time can be shortened thereby.

Figure 4:
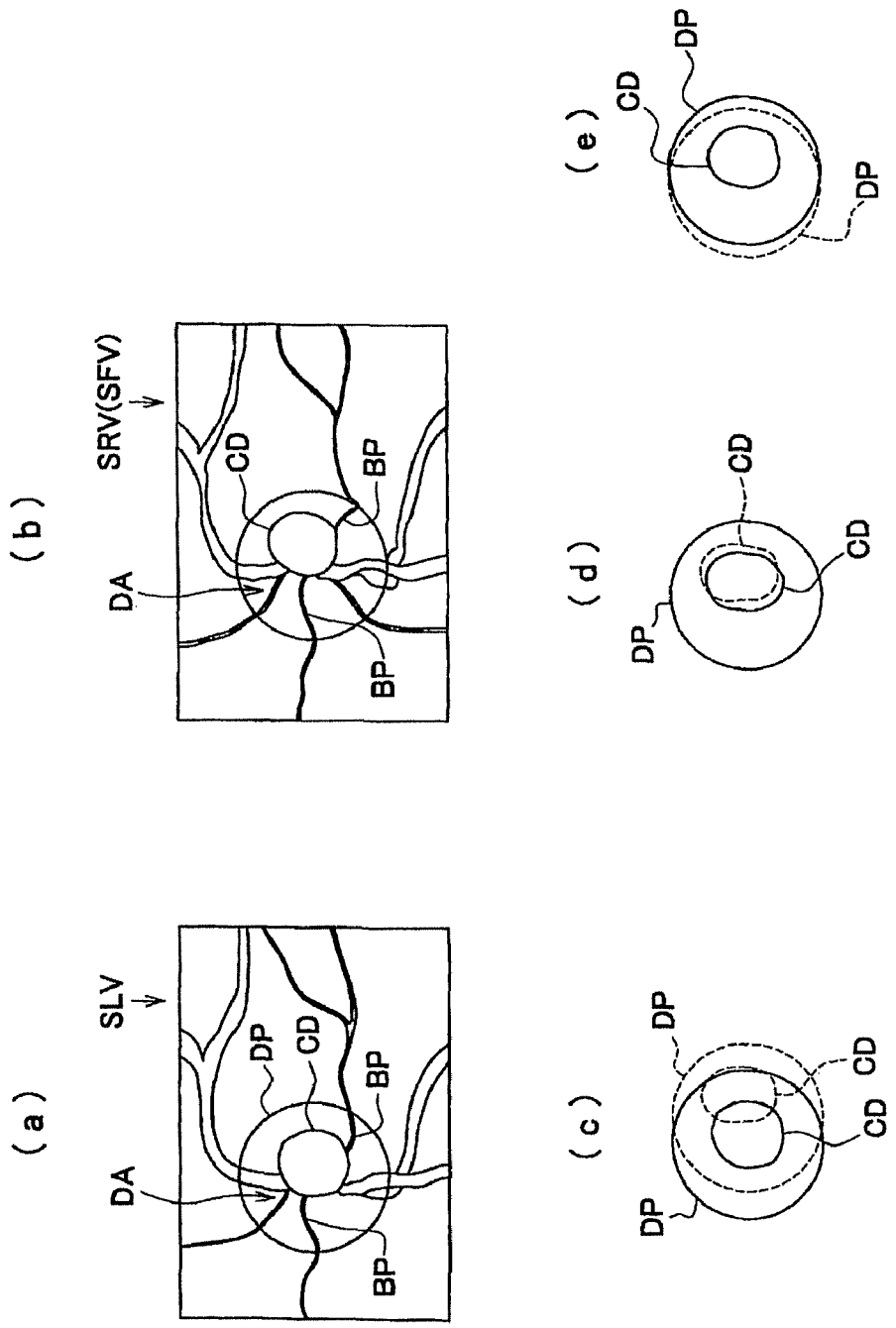
FIG. 4 are views typically showing shift of images of discs in both cases where discs of two stereo images are aligned or not aligned.

When the left stereo fundus image SLV, the right stereo fundus image SRV and the front fundus image SFV for some examined eye are stored in the memory area, the main control portion 2 instructs the DISC contour extracting portion 30 to extract contours DP of DISC from the respective images SLV, SRV and SFV as shown in FIG. 4 (a) and (b). The DISC area enclosed by the DISC contour DP has higher luminance than the peripheral area thereof (the part is shown in like white), so that the DISC contour extracting portion 30 extracts the pixels comprising the respective images SLV, SRV and SFV which luminance is higher than a constant value (is preferably stored in a proper memory in the DISC contour extracting portion 30 in advance as a threshold value for discriminating from the peripheral area of the disc portion that is darkly shown by statistically measuring luminance values of many fundus images in the DISC area DA), and judges the area of thus extracted pixels (almost circular shape) as the DISC area DA, and computes and determines the outer peripheral portion of the DISC area DA as the DISC contour DP. The DISC contour DP may be designated in such a way that the examiner manually designates a plurality of points corresponding to the DISC contour DP on the respective images SLV, SRV and SFV displayed on the display 6 through the input means, such as a mouse.

After obtaining the left stereo fundus image SLV, the right stereo fundus image SRV, the front fundus image SFV taken in such a state that the optical axis 26a of the eye ball 26 and the optical axis 17a of the objective lens 17 are corresponded with each other and these DISC contours DP for some eye to be examined and storing the obtained in a predetermined memory area, these fundus image data GDT are reproduced on the display 6 when a doctor operates the unit for obtaining and displaying fundus image 1 at a proper time, such as a time of obtaining informed consent from the examinee. At such a time, the doctor inputs the image reproduction instruction C2 and the identification number IDN of the examinee through the input portion 12. Receiving this, the main control portion 2 reads out the fundus image data GDT related with the identification number IDN and instructs the image playback portion 10 to reproduce such data GDT as three dimensional pseudo image.

In other words, the image playback portion 10 reads out the stored fundus image data GDT corresponding to the identification number IDN out of the image capturing portion 9 and outputs the read out on the display 6. At such a time, the image playback portion 10 repeatedly displays plural number of fundus image data GDT attaching the same identification number IDN thereto in order at predetermined time intervals, such as each one or two seconds.

Then, the left stereo fundus image SLV for some examined eye is firstly displayed on the display 6, and subsequently, the front fundus image SFV is displayed (if the front fundus image SFV has been obtained), and next the right stereo fundus image SRV is displayed and the front fundus image SFV is displayed again, and furthermore, the left stereo fundus image SLV is displayed. That is, continuous display cycle is executed. In other words, the images in the right/left direction are repeatedly reproduced and displayed in order with the front image as its center like a pendulum, such as the front image→the right image→the front image→the left image→the front image→the right image→the front image→the left image→the front image of the same examined eye.

The order of displaying respective images is optional. But, it is preferable to display both continuous images such that amount of shift between the optical axis 26a of the eyeball 26 and the optical axis 17a of the objective lens 17 is made as small as possible in order to prevent flickers of the image and express feeling of solidity. The image playback portion 10 controls such order of display based upon the stereo designation information DT2 showing relative positional relations between two or more fundus images.

When the image playback portion 10 thus reproduces the three dimensional pseudo images on the display 6, the person who watches the three dimensional pseudo image continuously sees the fundus images which view points are slightly different, and then the person feels as if the three dimensional image was displayed on the display 6, so that it is easy for the person to understand the fundus image.

When the three-dimensional pseudo image is displayed by continuously displaying the fundus images which view points are slightly different, a doctor who operates the unit for obtaining and displaying fundus image 1 can select display forms of the three dimensional pseudo fundus image through the input portion 12. That is, below-mentioned three indication modes are prepared as the display mode of the three dimensional pseudo fundus image that is reproduced by the image playback portion 10. A doctor can select the optional indication mode from the three kinds of indication modes through an operation of the input portion 12 so as to display the mode on the display 6. That is, as the three indication modes, (1) a normal indication mode wherein two or more fundus images having different positions of optical axis 17a, such as the front fundus image SFV, the left stereo fundus image SLV and the right stereo fundus image SRV, are alternately displayed on the display 6, (2) DISC base indication mode wherein two or more fundus images having different positions of optical axis 17a, such as the front fundus image SFV, the left stereo fundus image SLV and the right stereo fundus image SRV, are displayed on the display 6 on the basis of the DISC contour DP, and (3) CUP base indication mode wherein two or more fundus images having different positions of optical axis 17a, such as the front fundus image SFV, the left stereo fundus image SLV and the right stereo fundus image SRV, are displayed on the display 6 on the basis of blood vessels near CUP in the DISC area DA are prepared so as to be selectable through the input portion 12.

As shown in FIG. 4 (c), in the normal indication mode, the shift of the images due to the difference of the positions of the optical axes 17a of the respective fundus images is displayed as it is. Then, in the three dimensional pseudo fundus image displayed on the display 6, the DISC contours and the CUP contours between two fundus images continuously displayed are shifted by amount corresponding to the difference of the positions of the optical axes 17a of the respective fundus images in the right/left direction in the figure. The DISC contour DP and the CUP contour CD are formed in almost simple circle for easy understanding in FIG. 4, but these are not actual forms. In such a case, even if a doctor tries to extract the CUP contour CD through a mouse on the three dimensional pseudo fundus image displayed on the display 6 in the normal indication mode by designating two or more points on the CUP contour CD, it is difficult to designate on the three dimensional pseudo fundus image of the CUP contour CD since the DISC contour DP and the CUP contour CD are widely moved in the right/left direction in the figure.

When the image playback portion 10 repeatedly displays two or more fundus images on the display in order for the time set on each fundus image so as to produce the three dimensional pseudo image in the DISC base indication mode, the DISC contour DP of each fundus image is read out of a memory and two fundus images are displayed on the display 6 by changing the relative position of both fundus images so as to correspond the DISC contours DP between two fundus images continuously displayed with each other based upon the DISC contour DP of each fundus image extracted by the DISC contour extracting portion 30, as shown in FIG. 4 (d). By doing so, the positional shift of the optical axes 17a between two fundus images is made the smallest in the DISC contour DP part in appearance, and the amount of movement of the CUP contour CD that is positioned on back side rather than the DISC contour DP can be made small. When three or more fundus images are displayed in order, the fundus images are of course displayed on the display 6 so as to correspond all the DISC contours DP with each other by doing the above-mentioned procedures.

It is difficult to correctly correspond the DISC contours DP between two fundus images with each other. Then, two fundus images are shifted in the right/left direction in FIG. 4 (d) so that the total amount of pixels in the right/left direction sandwiched by the DISC contours of the two fundus images can be made the minimum. By doing so, the relative position of both fundus images continuously displayed is computed and determined, and both fundus images are displayed with the determined relative position.

In such a case, a doctor or the like is possible to easily extract the CUP contour CD on the three dimensional pseudo fundus image displayed in the DISC base indication mode on the display 6 by designating two or more points on the CUP contour CD through a mouse in comparison with the case of the normal indication mode. The CUP Contour extracting portion 31 computes and determines the CUP contour CD on the basis of thus extracted two or more points by performing interpolation on these points by a curved line, and displays the computed with a clear line on the fundus image (such as the fundus image SLV).

The CUP contour CD is displayed as a part having the highest luminance in the DISC area DA. But, the change of the luminance between the inside and the outside of the CUP contour CD (contrast) is smaller than the change of the luminance between the inside and the outside of the DISC contour DP, so that the operator is not almost puzzled by the movement of the DISC contour DP in the DISC base indication mode wherein the DISC contour DP is displayed with almost no movement of the DISC contour DP, and the operation of extracting the CUP contour CD is correctly executed thereby.

If the image playback portion 10 sets the longer display time on one fundus image of two fundus images continuously displayed than the other two fundus images and actually displays the fundus images, the operator generally inclines to designate the positions comprising the CUP contour CD based upon the CUP contour CD of the fundus image displayed for a longer time. Then, the operator can execute the operation of designating the positions comprising the CUP contour CD on the three-dimensional pseudo image without hesitating. In the designation of the positions on the three-dimensional pseudo image by the operator through the input portion 12, optional positions may be designated on the three-dimensional pseudo image in addition to the designation of the CUP contour CD. If the display time of one fundus image is set 0.5 second and 0.2 second is set as the display time of the other fundus image and the three-dimensional pseudo image is formed by alternately displaying both fundus images, the operator has a strong inclination to select and extract the positions comprising the CUP contour CD based upon the fundus image displayed for 0.5 second. Then, the CUP contour extracting portion 31 specifies the positions designated by the operator on the fundus image so as to compute and determine the CUP contour CD based upon the fundus image, the fundus image SLV for example having the longer display time, and displays the computed CUP contour CD on the fundus image having the longer display time as shown in FIG. 4 (a), for example. In a case where thee or more fundus images are displayed in order so as to produce the three-dimensional pseudo image, one fundus image of the three fundus images is displayed for a longer time than the other two fundus images and the operator may be invited to designate the CUP contour CD based upon the fundus image displayed for a longer time. Even in a case where the display time of the two or more fundus images continuously displayed is equal, when the CUP contour extracting portion 31 specifies the positions designated by the operator, the designated positions are computed based upon the specific fundus image, and the positions are displayed on the specific fundus image as the image (such as flushing points). Then, the positions designated by the operator are displayed on the specific fundus image of the plurality of fundus images continuously displayed as the image, so that the operator can further designate the position based upon the specific fundus image on which the positions are displayed. Therefore, the operator can easily execute the operation of designating the CUP contour CD thereafter without being puzzled by the other fundus images.

As shown in FIG. 4 (e) in the CUP base indication mode, the image playback portion 10 displays both fundus images on the display 6 so as to correspond the specific positions of corresponding blood vessels BP between two fundus images continuously displayed (that is, the blood vessel judged as the same blood vessel in two fundus images) with each other by changing the display form based upon the blood vessels BP near the CUP in the DISC area DA. In such a case, it is difficult to correctly correspond the specific positions of the blood vessels BP between two fundus images with each other. Therefore, the relative position of both fundus images at the time of continuous displaying is computed and determined by shifting the fundus images in the right/left direction of FIG. 4 (e) so that the total of the different pixels between the specific positions of the blood vessels BP between two fundus images can be made the smallest. In such a case, the positional shift of the optical axes 17a between both fundus images is made the smallest in appearance in the CUP contour CD portion, but the amount of the movement of the DISC contour DP positioned closer rather than the CUP contour CD is slightly large in comparison with the DISC base indication mode as shown in FIG. 4 (e). However, the amount of movement of the DISC contour DP can be made small in comparison with the normal indication mode.

Even in such a case, the operation of extracting the CUP contour CD with the mouse on the three-dimensional pseudo fundus image displayed on the display 6 in the CUP base indication mode through a doctor by designating a plurality of points on the CUP contour CD is easier than the case of the normal indication mode. However, the DISC contour DP moves in the right/left direction in the figure in comparison with the DISC base indication mode, so that the person may be puzzled by the moved DISC contour DP. Even in such a case, if one fundus image of two fundus images continuously displayed is displayed for a longer time than the other fundus image, an operator inclines to designate the points comprising the CUP contour CD based upon the CUP contour CD of the fundus image displayed for a long time. Then, the operator is not puzzled on the three-dimensional pseudo image, and can relatively easily execute the operation of designating the positions comprising the CUP contour CD.

The CUP contour extracting portion 31 computes and determines the CUP contour CD by executing curve interpolation on thus extracted points based upon these points, and the CUP contour CD is displayed on the fundus image, such as the fundus image SLV by a clear line segment, as shown in FIG. 4 (a).

The present invention is explained on the basis of the embodiment heretofore. The embodiments which are described in the present specification are illustrative and not limiting. The scope of the invention is designated by the accompanying claims and is not restricted by the descriptions of the specific embodiments. Accordingly, all the transformations and changes belonging to the claims are included in the scope of the present invention.

The invention claimed is:

1. Unit for obtaining and displaying fundus image, comprising:
    a display;
    a means for obtaining fundus image, having an objective;
    a memory means for storing a plurality of fundus images concerning the same eye to be examined, obtained through said means for obtaining fundus image, where positional relations between an optical axis of an eyeball of said eye to be examined and an optical axis of said objective are different from each other;
    an image playback portion for repeatedly displaying a plurality of fundus images stored in said memory means in order on said display for a time set on each said fundus image so as to produce a three-dimensional pseudo image;
    a CUP contour position designating means for designating a CUP contour position on said three-dimensional pseudo image that is displayed on said display;
    a position specifying means for specifying said CUP contour position designated on said three-dimensional pseudo image based upon a specific fundus image of said plurality of fundus images;
    a CUP contour computing means for computing a CUP contour based upon said specified CUP contour position; and
    a position displaying means for displaying said computed CUP contour on said specific fundus image.

2. The unit for obtaining and displaying fundus image according to claim 1, wherein said display time that is set on said specific fundus image is longer than one of the other fundus image.

3. The unit for obtaining and displaying fundus image according to claim 1, further comprising a DISC contour extracting means for respectively extracting DISC contours from said plurality of fundus images obtained through said means for obtaining fundus image and storing the extracted in said memory means;
    whereby said image playback portion:
        can produce the three-dimensional pseudo image by repeatedly displaying at least two fundus images on said display in order for the display time set on each fundus image; and
        has an image position determining means for determining a relative position of said two fundus images at the time when continuously displaying at least said two fundus images in order on the display so as to correspond the DISC contours between both fundus images continuously displayed with each other; and
    said image playback portion produces said three-dimensional pseudo image by displaying said both fundus images so as to correspond said DISC contours of both with each other based upon said relative position of both fundus images determined by said image position determining means.

* * * * *